United States Patent [19]

Sottiurai

[11] Patent Number: 4,840,940

[45] Date of Patent: Jun. 20, 1989

[54] METHOD FOR REDUCING THE OCCURRENCE OF DISTAL ANASTOMOTIC INTIMAL HYPERPLASIA USING FRACTIONATED HEPARIN

[76] Inventor: Vikrom S. Sottiurai, 5812 Virginia Pl., Metairie, La. 70003

[21] Appl. No.: 110,730

[22] Filed: Oct. 21, 1987

[51] Int. Cl.$^4$ ............................................. A61K 31/70
[52] U.S. Cl. ....................................... 514/56; 536/21; 623/1
[58] Field of Search ................. 514/56; 536/21; 623/1

[56] References Cited

U.S. PATENT DOCUMENTS

| | | | |
|---|---|---|---|
| 4,503,568 | 3/1985 | Madras | 623/1 |
| 4,546,499 | 10/1985 | Possis et al. | 623/1 |
| 4,717,719 | 1/1988 | Sportoletti et al. | 514/56 |

*Primary Examiner*—Johnnie R. Brown
*Assistant Examiner*—Jean C. Witz
*Attorney, Agent, or Firm*—Mortenson & Uebler

[57] ABSTRACT

A method is provided for reducing the occurrence of anastomotic intimal hyperplasia in grafts of artery, vein, biologic or synthetic conduits having end-to-side distal anastomosis. The method includes administering a regimen of fractionated heparin to the subject. Administration of the fractionated heparin can be either intravenously, intraperitoneally, subcutaneously or orally. Preferred dosage is 50–80 mg./kg. body weight per day.

9 Claims, 2 Drawing Sheets

METHOD FOR REDUCING THE OCCURRENCE OF DISTAL ANASTOMOTIC INTIMAL HYPERPLASIA USING FRACTIONATED HEPARIN

BACKGROUND OF THE INVENTION

This invention relates to a reduction of the occurence of intimal hyperplasia which can occur when autogeneous artery, vein, biologic or synthetic conduits are grafted in aorto-coronary, femoral-distal or any other bypass grafts of the body with distal end-to-side anastomosis. End-to-side anastomosis is preferred to end-to-end anastomosis in humans so that back perfusion to vital structures can be maintained. Although influenced by shear stress, turbulent flow and the compliance mismatch of the graft and host artery, this anastomosis configuration is performed out of necessity.

Human occluded femoral distal bypass grafts (Dacron® 7, PTFE-27, bovine-4, and vein graft-11, obtained from the Northwestern University, University of Michigan and Louisiana State University), removed at the time of the lower extremity revascularization, were studied. Distal anastomotic intimal hyperplasia was found to occur exclusively at the heel and the toe of the distal anastomosis and the floor of the host artery. Histocytologic analysis of the distal anastomotic intimal hyperplasia (DAIH) revealed an interlamination of smooth muscle cells and extracellular matrix. A similar morphologic architecture of the distal anastomotic intimal hyperplasia occurred in different types of grafts as reported in *Intimal Hyperplasia and Neointima: An Ultrastructural Analysis of Thrombosed Grafts in Humans*, Surg. 93:809-817, Sottiurai, V. S., Yao, J. S. T., et. al. Two forms of pathomorphogenesis were recognized in DAIH. Transformation of smooth muscle cells to myofibroblasts induced medial fibroplasia, whereas degeneration of smooth muscle cells progressed to medial necrosis. Smooth muscle cells seemed to play a role not previously recognized in the pathogenesis of the extracellular matrix leading to DAIH and graft occlusion.

Similar to human distal bypass grafts, DAIH in canine polytetrafluoroethylene (PTFE) grafts (n-42) in experimental studies occurred exclusively at the heel and the toe of the graft and the floor of the host artery ($P > 0.001$). Light microscopy and transmission electron microscopy (TEM) revealed the existence of a similar architecture of interlamination of cellular elements and extracellular matrix in DAIH. TEM further documented a gradual cell transformation and orientation from the graft to the lumen. The former was characterized by a gradual reduction of rough endoplasmic reticula with a concomitant acquisition of myofilaments, transforming ovoid mesenchymoid cells to slender myofibroblasts. The orientation of cells in DAIH was characterized by a random cell distribution at the periphery and a well organized interlamination of myofibroblasts with extracellular matrix near the lumen. DAIH is a biologic entity with active cellular and subcellular events. The biogenesis of DAIH appears to be influenced by the hemodynamics of blood flow at the distal anastomosis. See *Distal Anastomotic Intimal Hyperplasia in Human and Canine Bypass Grafts: An Ultrastructural Analysis*, J. Vasc. Surg. submitted for publication, Sottiurai, V. S., Batson, R. C., et al. One hundred and twenty ilio-distal bypasses were performed in dogs using standard (n-30) and thin wall (n-90) PTFE grafts. Fifty percent of the distal anastomoses had a Linton vein patch angioplasty to alter the compliance mismatch between a graft and the artery. Long-term follow-up (1-12 months) showed DAIH occuring at the heel and the toe of the distal anastomosis and the floor of the host artery. Vein patch angioplasty allegedly reduced the compliance mismatch at the distal anastomosis in standard PTFE graft and improved the patency rate by 60% over the standard PTFE graft without a distal vein patch angioplasty. Conversely, thin wall PTFE graft that has compliance comparable to dissected artery (scar tissue surrounding a dissected artery is known to reduce the compliance of the vessel) had a better patency rate (51%) than thin wall PTFE graft with a distal vein patch angioplasty. See *The Role of Vein Patch at Distal Anastomosis*, presented at the Southern Association for Vascular Surgery, Jan. 1986, Sottiurai, V. S., et al., submitted for publication.

Compliant differences between the PTFE graft and artery can present technical difficulty in small vessel anastomosis, as well as being implicated in late development of distal anastomotic intimal hyperplasia (DAIH). A distal autogenous vein patch permits precise suturing of the distal anastomosis and minimizes technical difficulty leading to early graft failure. Improvement of compliance mismatch of the PTFE graft and artery may impede the unwelcomed development of DAIH. The adjunctive use of a distal vein patch has resulted in excellent immediate graft patency in humans. See *Linton Patch Angioplasty: An adjunct to Distal Bypass with Polytetrafluoroethylene Grafts*, Ann. Surg. 199:684-1984, Batson, R. C., Sottiurai, V. S., et al.

Despite the absence of compliance mismatch in transpubic autogenous femoral-femoral bypass (n-20) with an end-to-side distal anastomosis and femoral interposition graft (n-20) with a distal end-to-end anastomosis, DAIH still occurred at the end-to-side anastomosis (100%) without graft occlusion and none at the end-to-end anastomosis ($P > 0.001$). Results of this experiment strongly suggested that, although prevention of compliance mismatch at the distal anastomosis would reduce the magnitude of DAIH formation, it could not prevent its occurrence. It is believed that the unanatomic and unphysiologic end-to-side distal anastomosis (an unnatural occurrence in primate vasculature) is responsible for the alteration of hemodynamics of blood flow at the distal anastomosis and for the occurrence of flow separation at the heel and the toe of the graft. The reverberation of blood flow and flow separation cause endothelial injury and allow the subendothelial smooth muscle cells to be influenced of leukocytes, monocytes and platelets. The latter two blood-borne substances are known to enhance smooth muscle cell migration, proliferation and extracellular matrix production which results in DAIH formation. See *Distal Anastomotic Intimal Hyperplasia: Biogenesis and Etiology*, presented at the Southern Association for Vascular Surgery, Jan. 1987, Sottiurai, V. S. et al., submitted for publication.

SUMMARY OF THE INVENTION

A method is provided for reducing the occurence of anastomotic intimal hyperplasia in grafts of artery, vein, biologic or synthetic conduits arteries having end-to-side distal anastomosis, the method including administering a regimen of fractionated heparin to a subject into which the graft has been implanted. The fractionated heparin may be administered orally, intravenously, intraperitoneally or subcutaneously. Preferably, the fractionated heparin is administered in divided doses daily in an amount between 50 and 80 mg./kg. body weight of the subject.

DETAILED DESCRIPTION OF THE INVENTION AND PREFERRED EMBODIMENTS WITH REFERENCE TO THE DRAWINGS

A method is provided for reducing the occurrence of anastomotic intimal hyperplasia in grafts of artery, vein, biologic and synthetic conduits having end-to-side distal anastomosis. The method includes administering a regimen of fractionated heparin to the subject. Administration of the fractionated heparin can be either intravenously, intraperitoneally, subcutaneously or orally. Preferred dosage is 50–80 mg./kg. body weight pre day. If administration of the fractionated heparin is stopped, distal anastomotic intimal hyperplasia will occur at the graft site.

Figure 1:
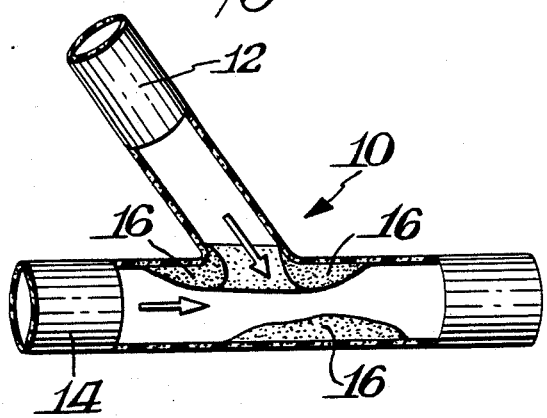
FIG. 1 is a schematic diagram, partly broken away, of an artificial vein grafted to a host artery having end-to-side distal anastomosis.

A detailed description of the invention is best provided with reference to the accompanying drawings wherein FIG. 1 is a schematic diagram, partly broken away, of a graft 10 wherein a vein graft 12 is sutured to host artery 14 with end-to-side distal anastomosis. The arrows indicate the direction of blood flow. Intimal hyperplasia 16 is indicated at the heel and the toe of the distal anastomosis and the floor of the host artery. Distal anastomotic intimal hyperplasia occurs exclusively at the heel and the toe of the graft and the floor of the host artery. It is believed that low shear stress and flow separation are responsible for the continuous endothelial injury at the heel and the toe of the distal anastomosis. Endothelial damage will predispose the underlying smooth muscle cells to the effect of platelet growth factor which is known to enhance smooth muscle cell migration, proliferation and extracellular matrix formation. Conversely, high shear stress is responsible for injury to the endothelial coverage of the floor of the host artery.

Figure 2:
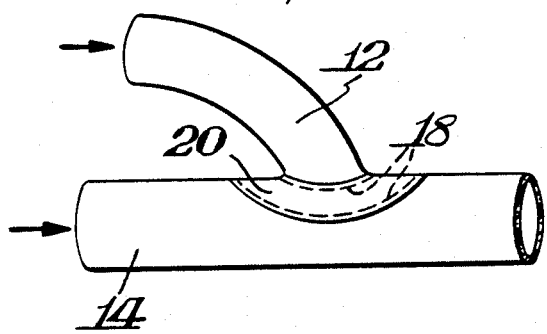
FIG. 2 is a schematic diagram of an artificial vein grafted to a host artery by vein patch angioplasty.

FIG. 2 is a schematic diagram of a vein graft 12 anastomized to host artery 14 by means of sutures 18 and vein patch 20.

Figure 3:
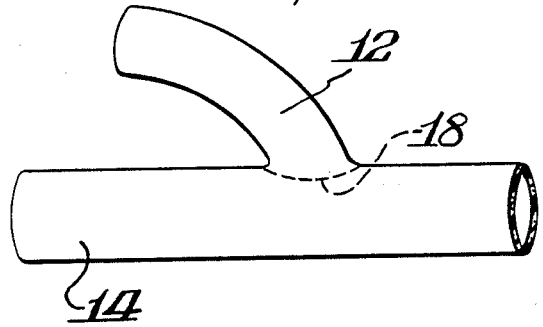
FIG. 3 is a schematic diagram of an artificial vein grafted directly to a host artery without distal patch angioplasty.

FIG. 3 is a schematic diagram of a vein graft 12 anastomized directly to a host artery 14 by sutures 18.

Figure 4:
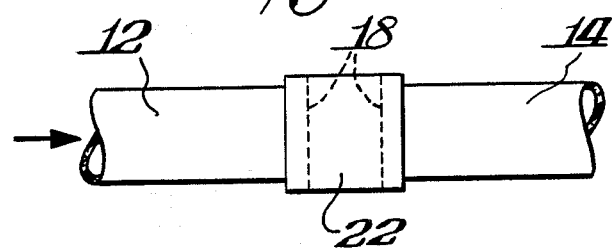
FIG. 4 is a schematic diagram of an artificial vein grafted to a host artery with a distal end-to-end anastomosis.

FIG. 4 is a schematic diagram of a vein graft 12 anastomized to a host artery 14 by means of sutures 18 and cuff 22.

Figure 4A:
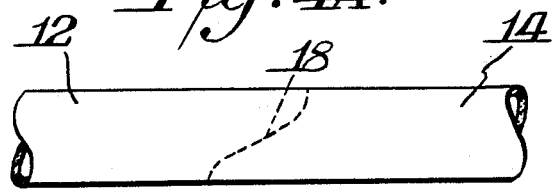
FIG. 4A is a schematic diagram of an alternate embodiment of an artificial vein grafted to a host artery with a distal end-to-end anastomosis.

FIG. 4A shows an alternate embodiment of a vein graft 12 anastomized to a host artery 14 by means of sutures 18.

Figure 5:
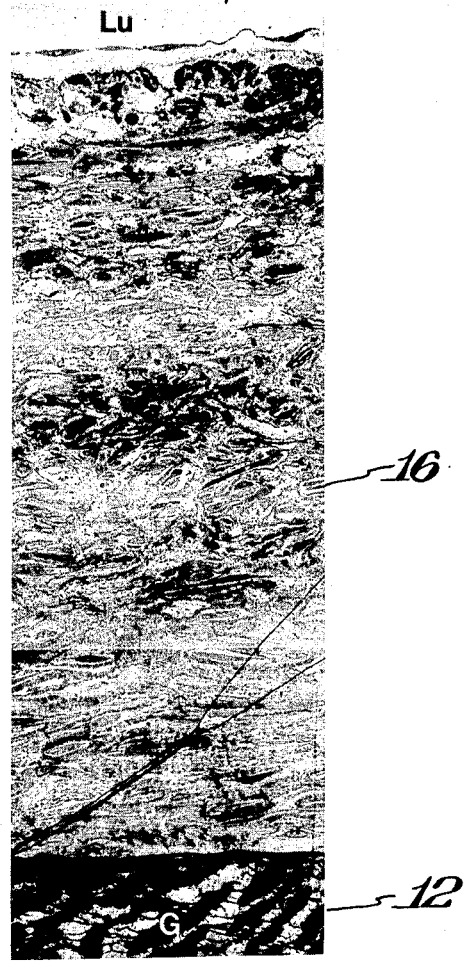
FIG. 5 is a transmission electron microscopic photograph of 80–130 cell thick distal anastomotic intimal hyperplasia adjacent an artificial graft at 450×magnification.

FIG. 5 shows a TEM taken at 450×magnification of 80–130 cell thick distal anastomotic intimal hyperplasia showing PTFE graft 12, intimal hyperplasia 16 and lumen 24. The 80–130 cell layers of myofibroblasts and smooth muscle cells are found interlaminated with the extracellular connective tissue matrix (predominately collagen fibers). The architecture of this histocytomorphology resembles the anatomy of the artificial wall. The luminal coverage is intact.

The occurrence of intimal hyperplasia was found exclusively at the heel and toe of the graft and the floor of the host artery in five different experimental and clinical studies outlined above.

Analysis of the histocytomorphology of intimal hyperplasia utilizing transmission electron microscopy revealed specific events in smooth muscle cell pathomorphogenesis of intimal hyperplasia as depicted in human and in animal studies. In human occluded grafts of all types (vein, Dacron ®, bovine, and PTFE), intimal hyperplasia in each graft had certain basic similarities. A laminated pattern of collagen fibers and cellular structure forms the basic architecture of intimal hyperplasia which resembles the anatomy of a muscular artery. Degenerating myocytes, active myofibroblasts and mesenchymal cells are the major cell population, while dense collagen fibers represent the dominant extracellular matrix of this pathologic entity. The myofibroblasts are modified smooth muscle cells. The cytoplasmic myofilament is displaced by the abundant rough endoplasmic reticula and Golgi complexes, orgenelles knows to synthesize proteinaceous substances.

A spectrum of morphologic transformation from cells resembling mesenchyme at the periphery to myofilament-laden myofibroblasts near the lumen exists in the intimal hyperplasia. Mitosis of the myofibroblast coupled with a gradual transformation from randomly distributed mesenchymoid cells near the graft fabric to the orderly aligned myofibroblast at the lumen strongly suggest the following:

a. DAIH is not a scar tissue but a viable biologic entity consisting of 80–130 cell thicknesses;
 b. DAIH undergoes a constant remodeling of its intrinsic architecture and external configuration dictated by the flow at the distal anastomosis.

The orderly interlamination of cell and extracellular matrix of the body of this 80–130 cell thick DAIH plus the abundant vasa vasoral network distributed throughout the DAIH not only resembles the anatomy of an arterial wall as seen in FIG. 5, but also supports the concept that DAIH is a viable biologic entity.

It is well recognized that the longevity and patency of the biologic and prosthetic graft are influenced by compliance mismatch of the graft and artery, shear stress, and turbulent flow. However, the persistence in intimal hyperplasia formation, despite a reduction of compliance mismatch (i.e., more compliant thin wall PTFE graft, Linton vein patch and the angle of the distal anastomosis to minimize turbulent flow, and shear stress plus autogenous femoral-femoral bypass) suggested that the distal anastomosis intimal hyperplasia formation is influenced by other hematologic factors. Smooth muscle cell proliferation at the anastomosis has been attributed to the influence of platelet growth factor in myocyte biogenesis. Suppression of smooth muscle cell response to platelet growth factor with heparin reduces smooth muscle cell proliferation and intimal hyperplasia formation. It has been established that fractionated heparin with O-sulfated, N-desulfated, and N-acetylated endings that lack an anticoagulant property also suppresses smooth muscle cell proliferation. When fractionated heparin was used preop intra-op, and post-op for only 3 weeks, suppression of smooth muscle cell or myofibroblast migration, proliferation, and extracellular matrix synthesis prevented intimal hyperplasia occurrence. In these experiments using dogs, carotid artery was endarterectomized to expose the medial smooth muscle cells. Brachial arteriotomy was made and the endothelial coverage was desiccated with a stream of air to destroy the endothelia in order to expose the underlying smooth muscle cells without mechanical injury to the smooth muscle cells per se. Illio-distal bypass using PTFE grafts were performed with end-to-side distal anastomosis to stimulate most of the human bypasses aorto-coronary, femoral, distal, aorto-femoral). Three weeks later, which was the time estimated necessary for endothelial regeneration in iliodistal bypass, similar operative procedures were done on the contralateral side of the same dog without the treatment of fractionated heparin to serve as the control. Data from these experiments consistently showed triphasic waveform in endarterectomized carotid and brachial artery in the fractionated heparin treated group and monophasic in the nonheparin treated group, which could be attributed to the thicker arterial wall in the carotid and brachial artery in the control group as demonstrated by the histologic study. These observations suggested that fractionated heparin prevents intimalmedial thickening by suppressing smooth muscle cell proliferation and matrix formation. However, DAIH subsequently occurred in bilateral ilio-distal bypass despite the limited fractionated heparin treatment. Computer digitization of the distal anastomosis revealed DAIH occurred exclusively at the heel and toe of the graft. Histologic study demonstrated an interlamination of myofibroblast with extracellular matrix resembling the histocytomorphology of DAIH found in other bypass grafts in human and canine studies. It is believed that end-to-side distal anastomosis is unphysiologic, unanatomic, and not a natural occurrence in the primate vascular system. Endothelial injury at the heel and the toe of the graft is therefore an inevitably continuous process in all end-to-side distal anastomosis as long as flow separation exists at the distal anastomosis. Unless a pharmacologic agent is administered continuously to suppress smooth muscle cell response to the platelet growth factor, smooth muscle cell proliferation and extracellular matrix formation will persist and so will the distal anastomotic intimal hyperplasia.

Heparin is a glycosaminoglycan (GAG) which contains N-sulfate groups. The N-sulfate groups are known to be important for anticoagulant activity of heparin. By partially modifying the N-sulfate groups, the anticoagulant activity of heparin preparations can be altered.

Previous methods of de-N-sulfation have been base on controlled hydrolysis in dilute acids, but this treatment usually results in some cleavage of the glycosidic linkages snd hydrolysis of O-sulfated groups. Recently, a new method for de-N-sulfation of heparin like GAG based on solvolysis in dimethyl sulfoxide has been reported. See *Selective N-desulfation of Heparin with Dimethyl Sulfoxide Containing Water or Methanol*, Carbohydr. Res. 46:87–95, 1976, Inoue, Y. and Nagasawa, K. This procedure was used under controlled conditions for partial de-N-sulfation. The partially de-N-sulfated heparin was N-acetylated with acetic anhydride and fractionated on a DowexA Cl column and a sepharose Cl-6B column to obtain the fraction with low anticoagulant activity but high antiproliferative activity.

Intimal hyperplasia in grafts of autogeneous vessels, biologic or artificial substitutes having end-to-side distal anastomosis has been found to be preventable by the administration of a regimen of fractionated heparin to a subject into which the graft has been implanted. By directly suppressing smooth muscle cells and myofibroblasts in synthesizing extracellular matrix, the fractionated heparin can prevent DAIH formation even though there is continuous endothelial injury resulting from flow separation due to the geometry of end-to-side anastomosis. The method includes administering a regimen of fractionated heparin to a subject before and after the graft has been implanted. The fractionated heparin may be administered intravenously, intraperitoneally, subcutaneously or orally, preferably in divided doses daily in an amount between about 50 and about 80 mg./kg. body weight of the subject.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A method for reducing the occurrence of intimal hyperplasia in grafts of substitute veins and arteries having end-to-side distal anastomosis, the method including administering a region of fractionated heparin to a subject into which said graft has been implanted, wherein said fractionated heparin is selected from the class consisting of fractionated heparin having O-sulfated, N-desulfated and N-acetylated endings.

2. A method of claim 1 wherein said fractionated heparin is administered orally.

3. The method of claim 1 wherein said fractionated heparin is administered intravenously.

4. The method of claim 1 wherein said fractionated heparin is administered intravenously.

5. The method of claim 1 wherein said fractionated heparin is administered subcutaneously.

6. The method of claim 1 wherein said fractionated heparin is administered daily in an amount between about 50 and about 80 mg./kg. body weight of said subject.

7. The method of claim 6 wherein said fractionated heparin is administered in divided doses daily.

8. The method of claim 1 wherein said graft is an autograft, allograft or xenograpft.

9. The method of claim 1 wherein said graft is a synthetic.

* * * * *

UNITED STATES PATENT AND TRADEMARK OFFICE
CERTIFICATE OF CORRECTION

PATENT NO. : 4,840,940
DATED : June 20, 1989
INVENTOR(S) : Vikrom S. Sottiurai

It is certified that error appears in the above-identified patent and that said Letters Patent is hereby corrected as shown below:

In the Specification:

In col. 4, line 11, please change "artificial" to --arterial--.

In col. 4, line 34, please change "knows" to --known--.

In col. 5, line 6, please change "preop" to --pre-op--.

In col. 5, line 19, please place --(-- before "aorto-coronary".

In col. 5, line 59, please change "base" to --based--.

In the Claims:

In claim 1, line 40, please change "region" to --regimen--.

In claim 4, line 50, please change "intravenously" to --intraperitoneally--.

In claim 8, line 60, please change "xenograpft" to --xenograft--.

Signed and Sealed this

Twenty-seventh Day of February, 1990

Attest:

JEFFREY M. SAMUELS

Attesting Officer　　Acting Commissioner of Patents and Trademarks